United States Patent [19]

Holmes

[11] Patent Number: 4,477,655

[45] Date of Patent: Oct. 16, 1984

[54] MOULDING OF POLY-HYDROXYBUTYRATE CONTAINING BACTERIAL CELL FRAGMENTS

[75] Inventor: Paul A. Holmes, Great Ayton, England

[73] Assignee: Imperial Chemical Industries PLC, Great Britain

[21] Appl. No.: 479,131

[22] Filed: Mar. 25, 1983

[30] Foreign Application Priority Data

Apr. 5, 1982 [GB] United Kingdom ............... 82 10004

[51] Int. Cl.³ .................... C08G 63/06; C08L 67/04
[52] U.S. Cl. .................................. 528/361; 106/124; 524/9; 524/17
[58] Field of Search ..................... 524/9, 17; 528/361; 106/218, 124

[56] References Cited

U.S. PATENT DOCUMENTS

| | | | |
|---|---|---|---|
| 3,036,959 | 5/1962 | Baptist | 528/361 X |
| 3,044,942 | 7/1962 | Baptist | 528/361 X |
| 3,107,172 | 10/1963 | Baptist et al. | 106/242 X |
| 3,275,610 | 9/1966 | Coty | 528/361 X |
| 4,101,533 | 7/1978 | Lafferty et al. | 528/361 X |
| 4,310,684 | 1/1982 | Vanlautem et al. | 528/361 X |
| 4,324,880 | 4/1982 | Dhien et al. | 528/361 X |
| 4,324,907 | 4/1982 | Senior et al. | 528/361 X |
| 4,358,583 | 11/1982 | Walker et al. | 528/361 X |
| 4,391,766 | 7/1983 | Barham et al. | 528/361 X |

*Primary Examiner*—Earl A. Nielsen
*Attorney, Agent, or Firm*—Cushman, Darby & Cushman

[57] ABSTRACT

Shaped articles can be made by extruding, or injection moulding, a composition containing at least 50% by weight of dried cells of a micro-organism containing a β-hydroxybutyrate polymer. In order to make the composition melt processable the cells are subjected to a cell wall breakage step before or after drying and, if necessary, are mixed with an extracted β-hydroxybutyrate polymer.

7 Claims, No Drawings

MOULDING OF POLY-HYDROXYBUTYRATE CONTAINING BACTERIAL CELL FRAGMENTS

This invention relates to moulding and in particular to moulding articles from β-hydroxybutyrate polymers.

Poly(β-hydroxybutyrate) is a thermoplastic polyester consisting of repeat units of the formula $$-CH(CH_3).CH_2.CO.O-$$

which is accumulated by many micro-organisms, particularly bacteria, for example of the genera Alcaligenes, Athiorhodium, Azotobacter, Bacillus, Nocardia, Pseudomonas, Rhizobium, and Spirillium, as an energy reserve material.

The polymer is conveniently prepared by cultivating the micro-organism in an aqueous medium on a suitable substrate, such as a carbohydrate or methanol, as an energy and carbon source. The substrate must, of course, be one that is assimilable by the micro-organism. In order to promote accumulation of the polymer, at least part of the cultivation is preferably conducted under conditions wherein there is a limitation of a nutrient that is essential for growth of the micro-organism but which is not required for polymer accumulation. Examples of suitable processes are described in EP-A-15669 and 46344.

Polymers containing both β-hydroxybutyrate units and other hydroxycarboxylic acid units, such as β-hydroxyvalerate acid units, can also be produced microbiologically. Thus a micro-biologically produced heteropolymer containing β-hydroxybutyrate and β-hydroxyvalerate residues is described by Wallen et al in "Environmental Science and Technology" 8 (1974) 576-9. Also, as described in EP-A-Specification Nos. 52459 and 69497 various copolymers can be produced by cultivating the micro-organism on certain substrates, such as propionic acid which gives rise to β-hydroxyvalerate units in the copolymer.

In the following description therefore by the term HB polymer we mean not only the homopolymer, poly(β-hydroxybutyrate) but also copolymers in which the β-hydroxybutyrate residues form at least 50 mole % of the polymer chain.

HB polymers can be extracted from cell suspensions by a variety of methods, generally involving a solvent extraction step. Methods that have been proposed include breakage of the cells by methods such as treatment with acetone, followed by solvent extraction of the HB polymer from the broken cells. Examples of such processes are described in U.S. Pat. Nos. 3,036,959 and 3,044,942 in which the solvents employed are pyridine or mixture of methylene chloride and ethanol. Other extraction solvents for PHB in the form in which it is produced in the bacterial cells include cyclic carbonates such as 1,2-propylene carbonate (see U.S. Pat. No. 4,101,533); chloroform (see U.S. Pat. No. 3,275,610); and 1,2-dichloroethane (see EP-A-15123).

U.S. Pat. No. 3,275,610 discloses other methods of cell breakage viz. ultrasonic vibration, grinding, French pressing, freezing/thawing cycles and lysozyme treatment, while, as described in the aforementioned European Patent Specification No. 15123, spray or flash drying of the suspension of cells renders them sufficiently permeable to enable the HB polymer to be solvent extracted.

In order to produce shaped articles from HB polymers it is generally necessary to employ an HB polymer that has been extracted from the micro-organism cells. However the extraction procedures significantly increase the cost of the product and so it would be desirable, where possible, to minimise the amount of extracted polymer employed.

For some applications however, high quality articles resulting from the use of extracted polymers are not necessary. An example of a use where a high quality is not required is a moulded seed tray or plant pot. Indeed it has been proposed in U.S. Pat. No. 3,107,172 to use dried bacterial cells containing poly(β-hydroxybutyrate) as a moulding material without any extraction step. We have found that, while such dried cells can be compression moulded, they have such a high viscosity, even at 190°-200° C. (above which temperature the polymer degrades), that they cannot be processed by other thermoplastics moulding methods, e.g. extrusion or injection moulding, involving significant flow of the polymer melt.

Applicants believe, although they do not wish to be bound by the theory, that the high viscosity resulting when no cell breakage step is employed is because the polymer granules are bound within the walls of the bacterial cells. Although the polymer melts at the moulding temperature, it is unable to flow as a result of the constraining influence of the bacterial cell walls.

In order that an HB polymer composition can be injection moulded or extruded, we have found that it is necessary that the melt flow time is not more than 15 minutes when assessed by the following procedure:

3.5 g of the composition are charged to the barrel of a melt flow grader (Daventest, Welwyn, England) provided with a die having a circular orifice of 2 mm diameter and 8 mm land length. The barrel is maintained at a temperature 10° C. above the melting point of the highest melting HB polymer in the composition, viz at 190° C. in the case where the HB polymer is β-hydroxybutyrate homopolymer. After a 5 minute warm-up period, a 10 kg load is applied to the piston, which has a weight of 0.16 kg. The melt flow time is the total time, including the 5 minute warm-up period, taken for a total of 2 g of the composition to be extruded through the die.

While dried cells can be used as a biodegradable filler in a composition containing an extracted HB polymer (which may be the same as, or different from, the HB polymer in the dried cells), in order to obtain a composition having a melt flow time of not more than 15 minutes, it is necessary that the composition contains at least 50% by weight of the extracted HB polymer. The use of such large amounts of extracted HB polymer is uneconomic for many applications because of the cost of the extraction process.

We have found that if the cells are subjected to a cell wall breakage step, before or after drying, then the amount of extracted HB polymer required to give a melt flow time of not more than 15 minutes to a composition containing a substantial amount of such dried, broken, cells can be reduced, and in some cases eliminated.

Accordingly the present invention provides a composition comprising at least 50% by weight of dried cells of a micro-organism containing at least 30% by weight of an HB polymer and 0 to 50% by weight of an extracted HB polymer, said dried cells having been subjected to a cell wall breakage step, before or after drying, such that said composition has a melt flow time of not more than 15 minutes.

The present invention also provides a method of making a moulded article comprising extruding or injection moulding a composition as aforesaid.

The micro-organism cells are produced in the form of an aqueous suspension. The cells have therefore to be separated from the suspension and dried.

While spray drying an aqueous suspension of cells containing a HB polymer renders the cell walls sufficiently permeable to permit the HB polymer to be extracted from the cells by means of a solvent, for example as described in the aforementioned European Patent Specification No. 15123, we have found that the use of such spray dried cells does not enable the amount of additional extracted HB polymer required to give a melt flow time of not more than 15 minutes to be significantly reduced.

It is therefore necessary to employ a method of cell wall breakage other than simply rendering the cells permeable to solvent as is the case with spray drying. Examples of suitable cell wall breakage steps include autolysis; digestion with hypochlorite, e.g. sodium hypochlorite; freezing/thawing cycling; lysozyme treatment; treatment with a solvent for cellular constituents (but not for the HB polymer)—acetone is such a solvent; or processes involving shearing of the cells, for example milling, homogenisation, French pressing, ultrasonic vibration, and, as described in EP-A-46335, heating the cell suspension to above 100° C. under pressure and then releasing the pressure by extrusion of the heated suspension through an orifice.

Autolysis of the cell walls by merely allowing the aqueous cell suspension to stand for a period of time is an effective method of cell wall breakage, particularly when used in conjunction with one or more subsequent cell wall breakage steps such as one of the other techniques described above. The amount of autolysis will depend on the amount of dissolved oxygen present in the cell suspension in relation to the amount of cells: hence the percentage of cells that undergo autolysis will decrease as the biomass concentration of the cell suspension increases unless the suspension is aerated. The rate of autolysis is such that the amount of autolysis is insignificant if the cells are dried within 10 hours of the removal of the cell suspension from the fermenter. Unless the suspension is aerated, e.g. by sparging with air, the amount of autolysis will not change significantly after about 3 days standing. Where the suspension has been allowed to autolyse by merely allowing it to stand for a few days, and then the cells are subjected to a further cell wall breakage step, little or no additional extracted HB polymer may be required to give a composition having a melt flow time of not more than 15 minutes. However, where no additional cell wall breakage step is employed after autolysis or where the amount of autolysis is insignificant and another cell wall breakage treatment is employed, the composition will generally need to contain 10 to 40% by weight of extracted HB polymer, although with particularly severe cell wall breakage processes, e.g. French pressing, no additional extracted HB polymer may be needed even if there is no autolysis.

A preferred cell breakage technique involves milling an autolysed cell suspension and then drying the milled suspension, e.g. by spray drying. Typically a 7% solids autolysed suspension is milled by a single pass through a commercial 'Dyno-mill' at a rate of 75 l/hr to give substantial cell fracture as seen by phase contrast microscopy.

Although the cell breakage process may be insufficient to give a melt flow time of not more than 15 minutes in the absence of additional, extracted, HB polymer, it is believed that the cell wall breakage enables the HB polymer within the broken cells to exert, when molten, some lubricating effect, thereby allowing the amount of extracted HB polymer required to be reduced.

The broken dried cells should contain at least 30% by weight of HB polymer for there to be any significant reduction in the amount of extracted HB polymer required. Preferably the dried broken cells contain at least 40, and in particular at least 50, % by weight of the HB polymer. The amount, if any, of additional extracted HB polymer required will depend on the HB polymer content of the dried broken cells and the severity of the cell breakage.

The composition should contain at least 50% by weight of the dried broken cells, and preferably contains at least 70% by weight. In addition to any extracted HB polymer that may be required the composition may also contain other materials such as an inert filler material such as calcium carbonate, silica or even dried cells of an HB polymer-containing micro-organism that have not been subjected to a cell wall breakage process.

In many cases the amount of extracted HB polymer required will be less than 30% by weight of the composition. The extracted HB polymer, if any, and any other ingredients may be mixed with the dried cells by conventional powder mixing processes.

The processing temperature required in an extrusion or injection moulding operation will depend on the nature of the highest melting HB polymer in the composition. With poly($\beta$-hydroxybutyrate), i.e. the homopolymer, a processing temperature of the order of 180°–200° C. is required. While the homopolymer has a melting point of the order of 180° C., copolymers generally have lower melting points, in some cases as low as about 120° C. and so, with copolymers, lower processing temperatures can, in some cases, be employed.

The invention is illustrated by the following examples.

EXAMPLE 1

An aqueous suspension of *Alcaligenes eutrophus* mutant S 301/C5 (NCIB 11599) was prepared by the method described in EP-A-46344 using glucose as the substrate and concentrated by centrifugation to a solids content of 54 g per liter. The cells had a poly ($\beta$-hydroxybutyrate) content of 60% by weight. The suspension was left standing at room temperature for four days after removal from the fermenter to allow autolysis to occur and then samples of the suspension were subjected to a variety of treatments:
  (a) The suspension was centrifuged at 5700 rpm for 15 minutes and the resulting pellets freeze dried.
  (b) The suspension was spray dried with inlet and outlet air temperatures of 240° and 110° C. respectively.
  (c) The suspension was milled by passing it through a "Dyno-mill" type KDS (Willy A. Bachofen, Switzerland) at a rate of 60 l hr$^{-1}$ and then spray dried as in (b).
  (d) The suspension was milled as in (c) and then centrifuged and freeze dried as in (a).

(e) The suspension was homogenised using an APV laboratory homogeniser model ISM-88A at an operating pressure of 34 MN m$^{-2}$ and then centrifuged and freeze dried as in (a).

(f) The suspension was French pressed in a French pressure cell press at an operating pressure of 10 MN m$^{-2}$ using a pressure cycle time of 30 minutes and then centrifuged and freeze dried as in (a).

(g) The suspension was sonicated using a DAWE Soniprobe type 7532A for 30 minutes at an output power of 110 watts, and then centrifuged and freeze dried as in (a).

(h) The suspension was frozen to $-18°$ C., then thawed to room temperature and then centrifuged and freeze dried as in (a).

(i) The suspension was centrifuged as in (a) to give a pellet which was then resuspended in acetone for 6 hours. The acetone was removed by filtration and then the cells dried in a vacuum oven.

The above procedures, with the exception of (e) were repeated on a similar cell suspension that had not been allowed to autolyse: the treatments and drying steps were carried out within 10 hours of the removal of the cell suspension from the fermenter.

The melt flow times were measured at 190° C. and are shown in the following table.

| Sample | Treatment | | Melt flow time (min) | |
|---|---|---|---|---|
| | Cell breakage | Drying | Autolysed | Non-autolysed |
| a | None | Freeze | 20* | >60** |
| b | None | Spray | >30* | >60** |
| c | Milled | Spray | 11 | >60* |
| d | Milled | Freeze | 14 | >60* |
| e | Homogenised | Freeze | 12.5 | — |
| f | French Pressed | Freeze | 12.5 | 14 |
| g | Sonicated | Freeze | 14 | 50* |
| h | Freeze/thawed | Freeze | 19* | >60* |
| i | Acetone washed | Vacuum oven | 14 | >60* |

In the case of the samples marked *, compositions containing 80% by weight of the treated cells and 20% by weight of extracted poly($\beta$-hydroxybutyrate) were made up and their melt flow times measured. In all cases the melt flow times were below 15 minutes.

In the case of the samples marked **, in order to give melt flow times below 15 minutes, the composition had to contain at least 50% by weight of the extracted poly($\beta$-hydroxybutyrate).

The extracted poly($\beta$-hydroxybutyrate) was obtained by solvent extraction from cells produced by spray drying the non-autolysed suspension.

The degree of cell breakage in the non-autolysed sample of run (f) was assessed by measuring the relative amounts of DNA in a sample of the French pressed suspension dissolved in the aqueous medium and remaining in the cells. The ratio of these measurements, which were made by a spectrophotometric technique following enzymatic treatment of the cell suspension, indicates the degree of cell breakage and was found to be 69%.

EXAMPLE 2

A larger sample of an autolysed suspension similar to that used in Example 1 was treated by the procedure (c) above except that the milling rate was 75 liters per hour. The dried cells again had a melt flow time of 11 minutes. The dried cells were extruded using a Betol 2520 extruder fitted with a 4 mm diameter die at a screw speed of 80 r.p.m. The thermostatted heaters along the barrel were set at 160° and 185° C. with the die zone at 190° C. It was found that the milled spray dried cells extruded as a continuous lace. The lace was relatively brittle but strong enough to feed through a water bath to crystallise the polymer and then to a pelletiser to granulate it.

EXAMPLE 3

A portion of the non-autolysed cell suspension as used in Example 1 was charged to a first stirred autoclave. A similar quantity of water was charged to a second stirred autoclave and heated under nitrogen pressure to 350° C. The first autoclave was pressurised with nitrogen to a pressure exceeding that in the second autoclave and then the contents of the first autoclave were forced into the second autoclave by the nitrogen pressure excess. The combined contents of the second autoclave were mixed vigorously for two minutes. The temperature of the combined contents of the second autoclave was approximately 150° C. but the applied pressure was sufficient to maintain the contents in the liquid state.

The contents of the second autoclave was then forced by the nitrogen pressure through a fine jet into a collection tank containing cold water.

The cells were collected by centrifugation and then freeze dried. The melt flow time was greater than 30 minutes.

A composition containing 80% by weight of the dried cells and 20% by weight of the solvent extracted poly($\beta$-hydroxybutyrate) as used in Example 1 had a melt flow time of 15 minutes.

EXAMPLE 4

The procedure of Example 3 was repeated using a suspension of cells of *Methylobacterium organophilum* (NCIB 11483) grown in an aqueous medium using methanol as the substrate and concentrated to a biomass content of 6.7% by weight by centrifuging. The cells contained about 40% by weight of poly($\beta$-hydroxybutyrate). The melt flow time of the dried cells was at least 60 minutes.

A composition containing 80% by weight of the dried cells and 20% by weight of the solvent extracted poly($\beta$-hydroxybutyrate) as used in Example 1 had a melt flow time of 15 minutes.

EXAMPLE 5

In this example the cell suspension employed was a non-autolysed suspension of *Alcaligenes eutrophus* (NCIB 11599) cells similar to that used in Example 1 but in which the cells contained about 40% by weight of poly($\beta$-hydroxybutyrate). Part of the suspension was centrifuged and freeze dried while the remainder was subjected to a cell wall breakage process as described in Example 3, and then centrifuged and freeze dried.

Compositions were then made up from the dried cells and varying amounts of the solvent extracted poly($\beta$-hydroxybutyrate) as used in Example 1, and their melt flow times measured.

The results were as follows:

| Composition (% by weight) | | Melt flow time (minutes) | |
|---|---|---|---|
| Dried cells | extracted polymer | Unbroken cells | Broken cells |
| 100 | 0 | >30 | >30 |
| 90 | 10 | — | >30 |
| 80 | 20 | >30 | 15 |

-continued

| Composition (% by weight) | | Melt flow time (minutes) | |
|---|---|---|---|
| Dried cells | extracted polymer | Unbroken cells | Broken cells |
| 70 | 30 | >30 | 12 |
| 50 | 50 | >30 | 10 |
| 40 | 60 | 15 | — |

I claim:

1. A process for the production of a shaped article comprising forming a composition containing (i) at least 50% by weight of dried cells of a micro-organism containing at least 30% by weight of a β-hydroxybutyrate polymer containing at least 50 mole % of β-hydroxybutyrate residues in the polymer chain, said dried cells having been subjected to a cell wall breakage process, before or after drying, and (ii) sufficient, if any, of an extracted β-hydroxybutyrate polymer containing at least 50 mole % of β-hydroxybutyrate residues in the polymer chain, such that the composition has a melt flow time, as herein defined, of not more than 15 minutes, and thereafter forming said shaped article by melt processing, extrusion or injection moulding, said composition.

2. A process according to claim 1 wherein said composition contains at least 70% by weight of said dried cells.

3. A process according to claim 1 wherein said dried cells contain at least 40% by weight of said β-hydroxybutyrate polymer.

4. A process according to claim 1 wherein said composition contains no extracted β-hydroxybutyrate polymer.

5. A process according to claim 1 wherein said dried cells are produced by subjecting an aqueous suspension of said micro-organism containing at least 30% by weight of said β-hydroxybutyrate polymer to a cell breakage step and thereafter drying said suspension.

6. A process according to claim 5 wherein the cell wall breakage process includes an autolysis step.

7. A process according to claim 6 wherein the cell wall breakage process comprises autolysis followed by a cell wall breakage step involving shearing of the cells.

* * * * *